United States Patent
Haswell et al.

(10) Patent No.: US 7,027,167 B2
(45) Date of Patent: Apr. 11, 2006

(54) DEPTH AND CONCENTRATION ESTIMATION

(75) Inventors: Stephen J. Haswell, Hull (GB); Paul D. I. Fletcher, Hull (GB); Xunli Zhang, Hull (GB)

(73) Assignee: Micro Chemical Systems Limited, Hull (GB)

( * ) Notice: Subject to any disclaimer, the term of this patent is extended or adjusted under 35 U.S.C. 154(b) by 82 days.

(21) Appl. No.: 10/179,023

(22) Filed: Jun. 26, 2002

(65) Prior Publication Data
US 2003/0016362 A1    Jan. 23, 2003

(30) Foreign Application Priority Data
Jun. 26, 2001    (GB)    ................................ 0115597

(51) Int. Cl.
*G01B 11/24* (2006.01)
(52) U.S. Cl. ..................... 356/630; 356/601; 356/237.6
(58) Field of Classification Search ........ 356/630–632, 356/433–436, 626, 237.6, 241.1, 601
See application file for complete search history.

(56) References Cited

U.S. PATENT DOCUMENTS

| 3,746,864 | A | * | 7/1973 | Tick et al. .................. 250/205 |
| 4,938,597 | A | * | 7/1990 | Gergely ....................... 356/614 |
| 5,309,213 | A | * | 5/1994 | Desjardins et al. ........... 356/70 |
| 5,438,417 | A |   | 8/1995 | Busch et al. |
| 5,465,153 | A | * | 11/1995 | Ladewski .................... 356/601 |
| 5,602,647 | A | * | 2/1997 | Xu et al. ..................... 356/435 |
| 5,777,731 | A | * | 7/1998 | McBride ................... 356/243.1 |
| 5,963,318 | A |   | 10/1999 | Held |
| 6,046,814 | A |   | 4/2000 | Karlsson et al. |
| 6,188,476 | B1 | * | 2/2001 | Hafeman et al. ............ 356/343 |
| 6,455,851 | B1 | * | 9/2002 | Lord et al. ................ 250/338.5 |
| 6,490,034 | B1 |   | 12/2002 | Woias et al. |
| 6,657,726 | B1 | * | 12/2003 | Wang et al. ................. 356/436 |

FOREIGN PATENT DOCUMENTS

| EP | 0 483 117 A2 | 4/1992 |
| EP | 0 634 642 A1 | 1/1995 |
| JP | 57-156542    | 9/1982 |
| JP | 8-313429     | 11/1996 |
| WO | 98/228033    | 5/1998 |

* cited by examiner

*Primary Examiner*—Richard A. Rosenberger
(74) *Attorney, Agent, or Firm*—Leydig, Voit & Mayer, Ltd.

(57) ABSTRACT

A method of estimating dimensions of an opening (36) in a body (26) comprises filling the opening (36) with a fluid that absorbs an electromagnetic radiation (40). The radiation (40) is transmitted through the body (26) and through the fluid in the opening (36). The intensity of the electromagnetic radiation, after transmission through the fluid, is determined at an area that corresponds to a radiation path through the fluid in the opening. The intensity is used to determine the absorbance of the fluid in the radiation path and consequently the length of the radiation path.

In an alternative method, when the depths of the opening are already known, the intensity is used to determine concentration of a chemical in the opening.

28 Claims, 6 Drawing Sheets

DEPTH AND CONCENTRATION ESTIMATION

The invention relates to a method of estimating dimensions of an opening in a body. Additionally, the invention relates to a method of monitoring concentration of a chemical in a fluid filling an opening in a body.

A known body is a chip-type micro-reactor used, for example, for performing chemical reactions. The micro-reactor is formed from a base plate and an upper block. A plurality of interconnected grooves are etched in an upper surface of the base plate and this upper surface is then thermally bonded to a lower surface of the upper block. Hence, the lower surface of the upper block closes the grooves so as to form a plurality of interconnected channels in the micro-reactor. Reagents are moved through, and react within, these channels.

In order to understand fully the movement and reaction of reagents in a micro-reactor, it is necessary to know the dimensions of the channels in the micro-reactor. It is relatively easy to determine the dimensions of the grooves, before the base plate and the upper block are bonded together. However, it is possible, or even likely, that the dimensions will change during the bonding process.

Once the upper block and the base plate have been bonded together, the dimensions of the channels can be determined by cutting the micro-reactor, so as to reveal the channels in cross-section. However, this clearly destroys the micro-reactor. Moreover, it is extremely difficult to obtain a clean cut without chipping the micro-reactor around the edges of the channels.

According to a first aspect of the invention, there is provided a method of estimating dimensions of an opening in a body comprising, filling the opening with a fluid that absorbs an electromagnetic radiation, transmitting said electromagnetic radiation through the body and through the fluid in the opening, determining an intensity of the electromagnetic radiation, after transmission through the fluid, at an area corresponding to a radiation path through the fluid in the opening, and using said intensity to estimate the length of said radiation path.

This method allows dimensions of openings in a body to be estimated in a non-destructive manner.

Additionally, it is desirable to be able to monitor concentration of chemicals in the channels of a chemical reactor.

According to a second aspect of the invention, there is provided a method of monitoring concentration of a chemical in a fluid filling an opening in a body, the chemical absorbing an electromagnetic radiation, comprising transmitting said electromagnetic radiation through the body and through the fluid in the opening, determining respective intensities of the electromagnetic radiation, after transmission through the fluid, at a plurality of areas corresponding to respective radiation paths through the fluid in the opening, and using said intensities to estimate respective concentrations of the chemical in the radiation paths.

The following is a more detailed description of embodiments of the invention, by way of example, reference being made to the appended schematic drawings in which.

Figure 1:
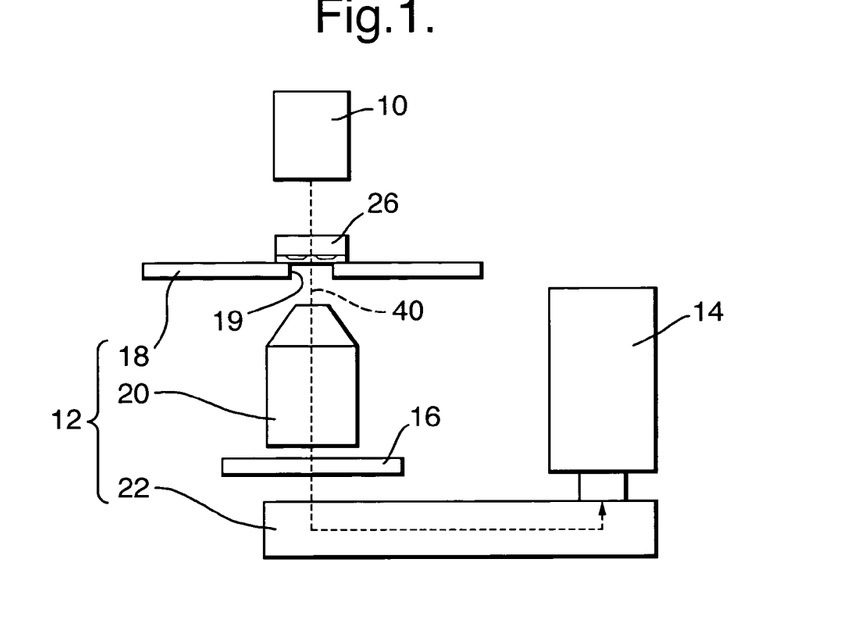
FIG. 1 shows an apparatus suitable for estimating dimensions of channels in a micro-reactor.

An apparatus suitable for estimating dimensions of channels in a chip-type micro-reactor is shown in FIG. 1. The apparatus comprises a tungsten lamp 10, a microscope 12, a CCD camera 14 and a narrow bandpass filter 16.

The tungsten lamp 10 has a power rating of 100 W and emits light over the wavelength range from approximately 400 nm to approximately 800 nm.

The microscope 12 includes a microscope stage 18 and an objective lens 20, which may have a magnification of, for example, 1.5× or greater. Additionally, the microscope 12 includes a structure 22 that houses optics allowing an image to be directed either to the camera 14 or to an eye-piece (not shown).

The camera 14 is a digital monochrome CCD camera (Hamamatsu C4742-95-12NRB). The camera gives a digital output of 1024×1024 pixels with 12 bit resolution of the light intensity in each pixel. The camera is connected to a personal computer (not shown) and controlled by the digital image recording and analysis software AQM from Kinetic Imaging Ltd.

The narrow bandpass filter 16 is an Edmund Scientific N43-136 filter having a transmission peak at 649 nm and a full width at half maximum absorbance of 11 nm. The transmission spectra of the bandpass filter 16 is shown at 24 in FIG. 2.

The tungsten lamp 10, the microscope 12, the camera 14 and the bandpass filter 16 are covered by a hood (not shown) to exclude or reduce ambient light.

The arrangement is such that light from the tungsten lamp 10 passes through an aperture 19 in the microscope stage 18 into the objective 20 of the microscope, and then through the narrow bandpass filter 16 and into the structure 22. Within the structure 22 light is directed into the camera 14 (or can be directed to the eye-piece if required). A sample can be positioned on the stage 18 in the light path between the tungsten lamp and the objective 20 so that an enlarged, transmission image of a sample can be recorded by the camera 14.

The camera 14 and the digital image recording and analysis software are set up so that the camera output pixels are grouped into groups of 16 pixels (squares of 4 pixels×4 pixels) so as to give a square output array of 256×256 groups. For each group, separate light intensities of the constituent 16 camera output pixels, measured by the camera 14, are averaged to give a single mean intensity value. This arrangement, which is also known as "4×4 binning", provides a good compromise between rapid data acquisition, signal-to-noise ratio, spatial resolution and data file size.

Scion Image software (Scion Corporation) is used to transfer the mean intensity value of each group of the 256×256 output array into Microsoft EXCEL, which is used for performing calculations utilising the values.

Use of the apparatus to estimate dimensions of channels 36 in a chip-type micro-reactor 26 will now be described.

Figure 3:
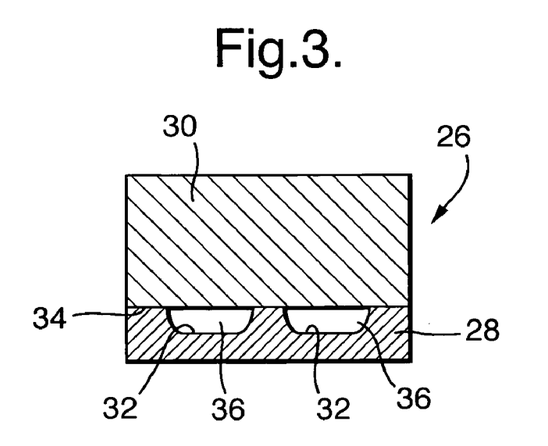
FIG. 3 is a cross-sectional view (not to scale) of part of a micro-reactor.

The micro-reactor 26 is shown in FIGS. 1 and 3 and is of known type. The micro-reactor 26 has a base plate 28 that is formed of glass and that has a thickness of about 2 mm (the height of the base plate 28 as shown in FIG. 3). A plurality of interconnecting grooves (two of which are shown at 32 in FIG. 3) have been etched into the upper surface of the base plate 28 using known methods. The grooves 32 have a width of approximately 450 μm and are exaggerated in size in FIGS. 1 and 3 for clarity. The micro-reactor 26 also has an upper block 30 having a lower surface 34 that has been thermally bonded to the upper surface of the base plate 28 in a known manner. Hence, the lower surface 34 of the upper block 30 closes the grooves 32 so as to form the channels 36. Additionally the upper block 30 has a plurality of cylindrical apertures (not shown) extending between its upper and lower surfaces. These apertures connect with the channels 36 and serve as reservoirs for liquids.

In order to estimate the dimensions of the channels 36, a dye solution and a reference solution are prepared. The reference solution is simply the solvent (in the absence of any dye) in which the dye is dissolved in the dye solution. In this example, the reference solution consists of 30.2 weight % glycerol in m-cresol. The dye solution is a solution of the dye Patent Blue in the reference solution.

Dissolving the Patent Blue dye in the glycerol/m-cresol solvent may require treatment in an ultrasonic bath for several hours. Once the Patent Blue dye has fully dissolved, the absorbance of the dye solution is measured in a spectrophotometer using cuvettes of known path length. Given that the extinction co-efficient of Patent Blue is known, the precise concentration can be determined using the equation:

$$A = Cd\epsilon.$$

Where A is absorbance,

C is concentration, d is path length, and $\epsilon$ is the extinction co-efficient of Patent Blue.

In the current example, the concentration of the Patent Blue in the dye solution is 0.8275 mM. Factors that influence the choice of Patent Blue concentration in the dye solution are discussed below.

Figure 2:
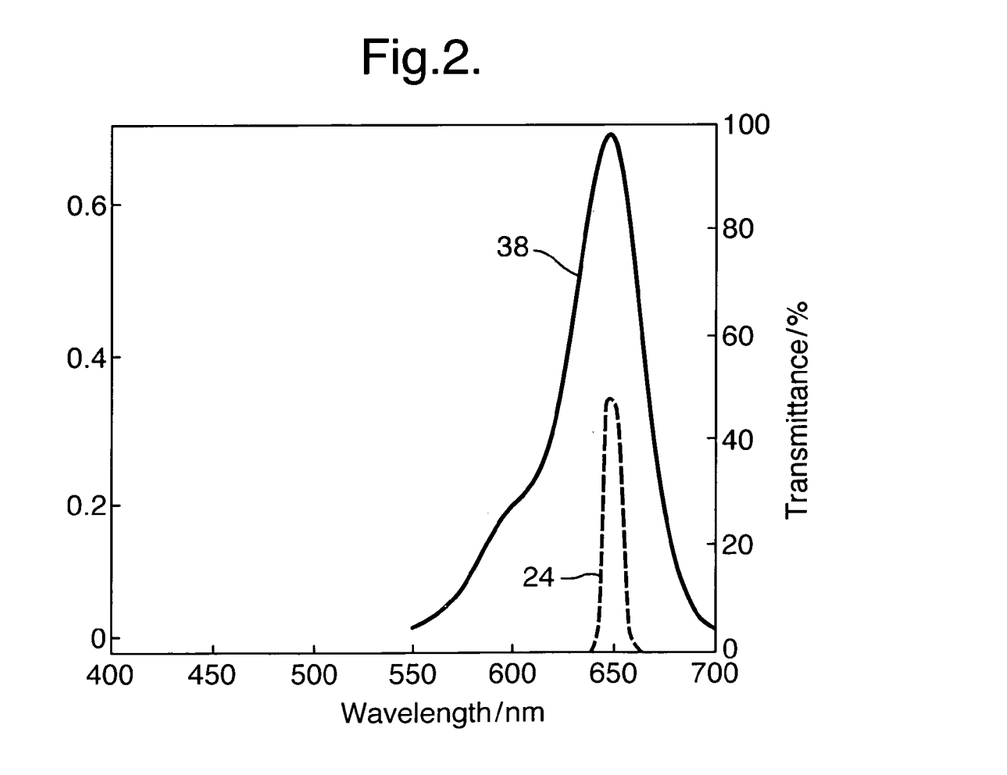
FIG. 2 shows absorbance of a solution of Patent Blue and transmittance of a narrow bandpass filter.

The absorption spectrum of the dye solution is shown at 38 in FIG. 2. As shown in FIG. 2, the absorption maximum of the dye solution (approximately 647 nm) corresponds closely to the transmission spectrum of the bandpass filter 16.

The micro-reactor 26 is then clamped immovably to the stage 18 of the microscope 12 so that the channels 36 lie in the path 40 of light travelling from the tungsten lamp 10 to the objective 20. As shown in FIG. 1, the micro-reactor 26 is positioned on the stage 18 with the upper block 30 above the base plate 28 and so that light from the tungsten lamp 10 passes through the micro-reactor 26 and generally normal to the lower surface 34 of the upper block 30. The position is such that the camera 14 together with the digital image recording and analysis software can record images of a portion (approximately 8×8 mm) of the micro-reactor 26—the portion containing a plurality of channels 36. As indicated above, each such image is made up of a 256×256 array of mean intensity values (each mean intensity value being the average intensity value of 16 camera output pixels, as described above). As will be appreciated, each mean intensity value corresponds to the intensity of light that has passed through a different part of the imaged portion of the micro-reactor 26.

The reference solution is then introduced into the micro-reactor 26 so as to fill the channels 36 for which the dimensions are to be estimated.

The resolution of the system is then standardised and optimised. Each mean intensity value (of a 16 pixel group as described above) is measured on a linear scale of zero to 4095 arbitary units. It is desirable, in this system, for the mean intensity values corresponding to light passing through the channels 36, when the channels 36 are filled with the reference solution, to be about 3500 on the above mentioned scale. Additionally, it is desirable for the mean intensity values to be about 100 on the above mentioned scale when the tungsten lamp 10 is switched off—the values of approximately 100 then largely correspond to system noise. The gain of the camera 14 and the intensity of the light emitted by the tungsten lamp 10 are adjusted so as to obtain the desired values of 3500 and 100. This serves the purpose of both standardising and maximising the resolution of the system.

Once the resolution has been standardised and optimised as discussed above, the camera 14 and the digital image recording and analysis software are then use to record an image of the micro-reactor 26 while the channels 36 are filled with the reference solution and while the micro-reactor 26 is illuminated by the tungsten lamp 10. This image is referred to below as the reference solution image.

Then, without moving the micro-reactor 26, the tungstem lamp 10 is turned off and a further image is taken. This image is referred to below as the dark image and the mean intensity values that make up the dark image generally correspond to system noise.

After the dark image has been recorded, the reference solution is removed from the channels 36 of the micro-reactor 26 and the channels 36 are filled with the dye solution. The replacement of the reference solution with the dye solution takes place while the micro-reactor 26 remains clamped in the same position used for the reference solution image and for the dark image. The solutions can be changed using syringes.

Once the channels 36 have been filled with the dye solution a third image of the micro-reactor 26 is taken. This third image is referred to below as the dye solution image.

Hence, the camera 14 and the image recording and analysis software are used to obtain three images, the reference solution image, the dye solution image and the dark image. Each of these images is formed by a 256×256 array of mean intensity values. Each mean intensity value is an average value of the light intensity that has fallen on a respective square (4×4 camera pixel) area of the camera 14. Hence, each mean intensity value is a measure of the intensity of light that has passed along a respective light path, through the micro-reactor 26, that is generally square in cross-section. As the micro-reactor 26 remains in the same position, relative to the tungsten lamp 10, the microscope 12 and the camera 14, during recording of the three images, corresponding mean intensity values in the dye solution and reference images give the intensity of light that has passed through identical light paths through the micro-reactor 26, when the channels 36 have been filled with either the dye solution or the reference solution respectively. The dark image also has mean intensity values that correspond, in terms of the different regions of the micro-reactor 26, to the mean intensity values of the dye and reference solution images, although clearly light does not pass through the micro-reactor 26 while the dark image is recorded.

Accordingly, by comparing corresponding mean light intensity values from the dye solution image, the reference solution image and the dark solution image, all of which corresponding to the same 4×4 pixel area in the camera 14, which in turn receives light that has passed through a generally square cross-section light path extending through a channel 36, it is possible to determine the absorption of light that is attributable to the dye (in the dye solution image) that lies within the light path in the channel 36. As the concentration of the dye in the dye solution has been precisely determined, and as the extinction co-efficient of the dye is known, it is possible to calculate the length of the generally square cross-section light path extending through the channel 36. This is done by using the following equation:

$$\log\left(\frac{I_{ref} - I_{dark}}{I_{sol} - I_{dark}}\right) = Cd\varepsilon$$

wherein $I_{ref}$ is a mean intensity value from the reference solution image;

$I_{sol}$ is the corresponding mean light intensity value from the dye solution image;

$I_{dark}$ is the corresponding mean intensity value from the dark image;

C is the concentration of the dye in the dye solution in mol $dm^{-3}$; and $\varepsilon$ is the extinction co-efficient in mol$^{-1}$ dm$^3$ μm$^{-1}$.

The value of d is the length in μm of the light path extending through the channel 36—that is to say the light path extending between the lower surface 34 of the upper block 30 and the upper surface of the base plate 28.

As indicated above each of the images consists of an array of 256×256 mean intensity values (65,536 mean intensity values in total for each image). The same calculation is performed for each triplet of corresponding mean intensity values (i.e. corresponding mean intensity values from the dye solution image, from the reference solution image and from the dark image).

Figure 4:
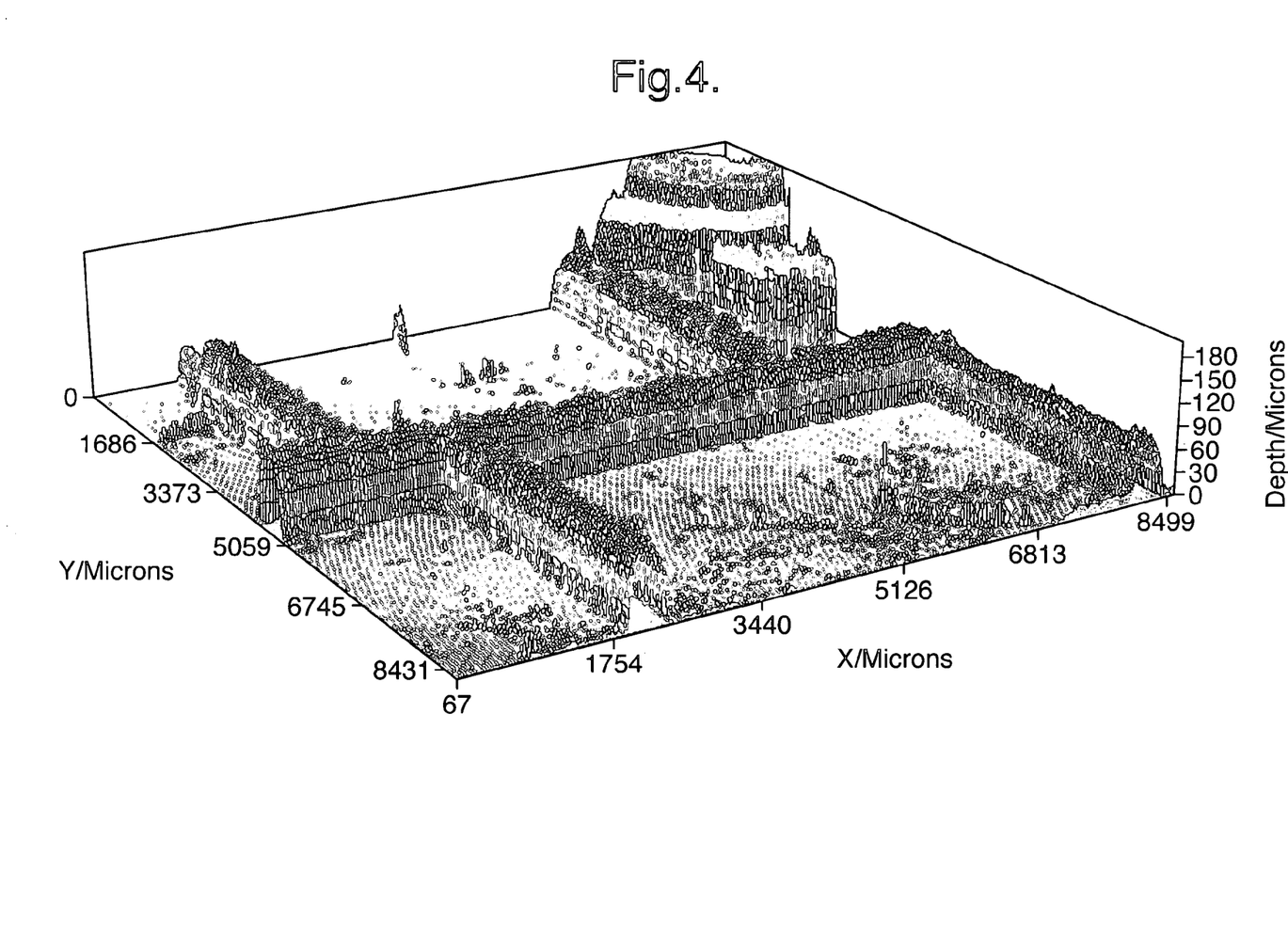
FIG. 4 shows an array of 256×256 depth measurements.

FIG. 4 shows the results of such an analysis. FIG. 4 is an array of 256×256 depth values that have been determined as described above. The array corresponds to an area of the micro-reactor 26 that is approximately 8 mm by 8 mm. As can be seen in FIG. 4, this area contains parts of five channels 36. As can be seen in FIG. 4, the depths of the channels 36 at a plurality of positions in the channels 36 are determined.

On the assumption that the planar lower surface 34 of the upper block 30 remains planar during the thermal bonding process when the micro-reactor is made, FIG. 4 shows not only the depths at different regions of the channels 36, but also shows the shapes of the channels 36 (the planar base of the graph corresponding to the planar lower surface 34).

The same method has been used to study the depths of openings of known sizes in commercially available capillaries and in a 1 mm path length cuvette. The depths obtained using this method were found to correspond closely to the known dimensions of the openings.

Figure 5:
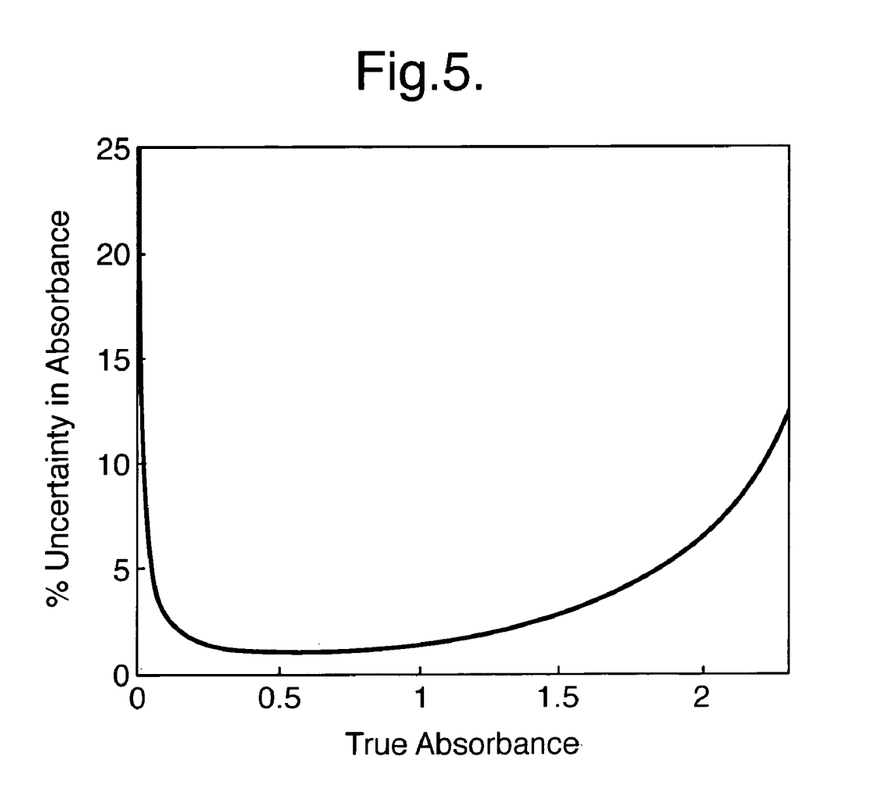
FIG. 5 is a graph showing percentage uncertainty in absorbance plotted against true absorbance.

FIG. 5 shows the relationship between the percentage uncertainty in absorbance measurements, in the method described above, plotted against true absorbance. It will be seen that the minimum uncertainty, about 2%, is obtained with absorbance values of about 0.6. Accordingly, where the above method is to be used to estimate dimensions of a channel for which the dimensions are approximately known, the concentration of the dye in the dye solution can be adjusted to give absorbance readings near 0.6. This helps to increase the accuracy of dimensions estimated using the method described above.

In the example described above, the dye solution and the reference solution were chosen so as to optimise the method, bearing in mind the following factors. Firstly, the dye solution and the reference solution have a refractive index that is closely matched to the glass of the micro-reactor 26. Clearly, when the method is used to estimate dimensions of openings in bodies made of other transparent materials, dye and reference solutions can be chosen so that they are matched to the refractive index of the transparent body.

Other advantageous features of the dye solution and of the reference solution are as follows. Firstly, the solutions are not volatile at room temperature. Secondly, the dye, Patent Blue, is highly soluble in the reference solution and this allows sufficiently high absorbances to be obtained, despite the relatively short dimensions (path lengths) of the channels 36. Thirdly, the dye solution described above obeys the Beer-Lambert Law closely. Fourthly, the dye and reference solutions are chemically stable. Finally, the absorbance of the reference solution is negligible compared to that of the dye solution at the optimum wavelength (about 649 mm as described above).

Figure 6:
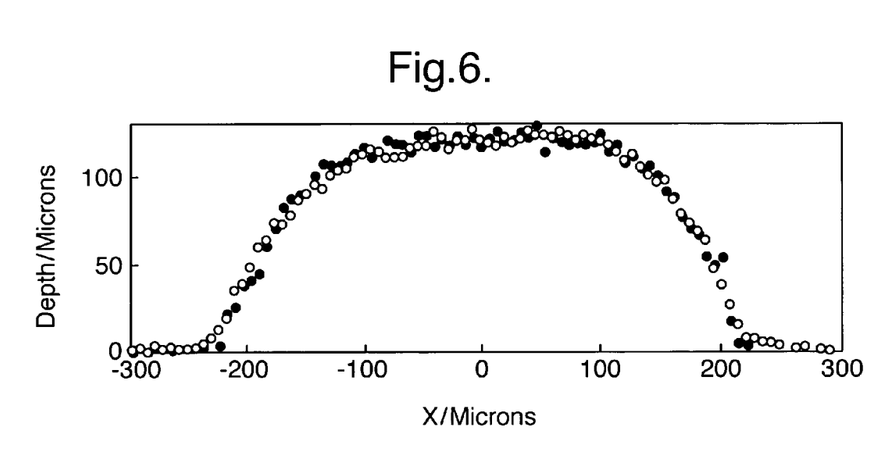
FIG. 6 is a graph showing depth measurements at a cross-section through a channel in a micro-reactor.

In order to determine whether it is strictly necessary to match the refractive index of the dye and reference solutions to that of the body under study, the micro-reactor 26 described above was also studied using a different combination of dye and reference solutions. In this example, the dye Rose Bengal was dissolved in water to form the dye solution. The reference solution was water alone. These alternative reference and dye solutions were used to determine depths of the channel 36 in the micro-reactor 26 in exactly the same way described above. FIG. 6 shows depth measurements obtained using this method with either the Patent Blue dye solution and the corresponding reference solution (open circles) and with the Rose Bengal dye solution and corresponding reference solution (solid circles), at the same cross-sectional position in a channel 36. As can be seen from FIG. 6, the depth values obtained corresponded closely using the two pairs of solutions. The refractive index of the glass of the micro-reactor 26 is approximately 1.52. The refractive indices of the Patent Blue dye solution and the corresponding reference solution are the same. However, the refractive indices of the Rose Bengal dye solution and the corresponding reference solution (which are aqueous) are approximately 1.33. FIG. 6 suggests that the difference in refractive indices between the aqueous solutions and the glass is not sufficient to distort the depth measurements obtained. However, it is possible that greater differences in refractive indices would cause distortion.

Figure 7:
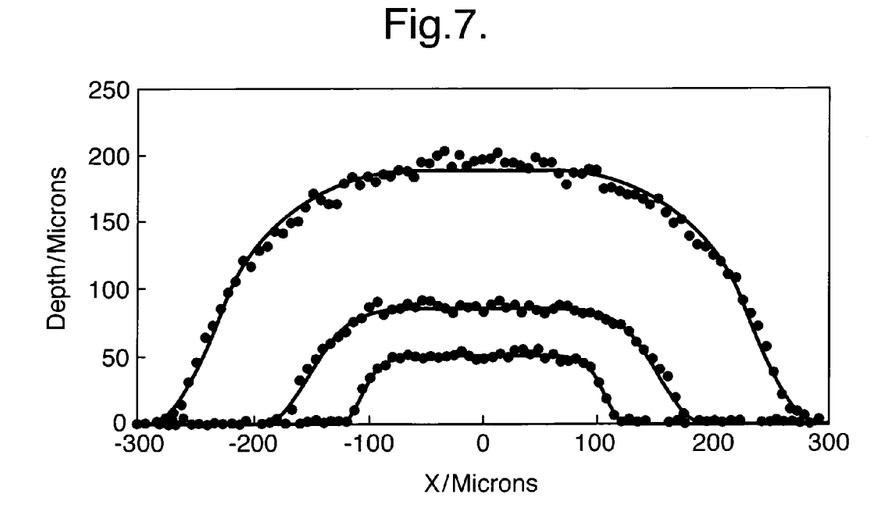
FIG. 7 shows depth measurements at cross-sections through three different channels in a micro-reactor.

FIG. 7 shows three sets of depth measurements, corresponding to cross-sections through three separate channels in micro-reactors. As can be seen from FIG. 7, the dimensions of the three channels are considerably different. FIG. 7 also shows best fit lines obtained using a mathematical model of the etching process by which the channels are formed.

For many etching processes which use etching solutions, etching proceeds at equal rates in all directions. In other words, the etching is isotropic. The etch depth d is controlled by the etch conditions and the etch time. Ideal isotropic etching through a channel mask of width m is expected to produce a channel profile comprising a rectangular shape of width m and depth d bounded by two quarter circle edges of radius equal to d. The expected channel width at the glass surface is equal to (m+2d). In practice, either prolonged etching or thermal bonding may produce a "smoothing" of the channel edges away from the idealised quarter circle shape. In order to model the channel profiles, the ideal isotropic etch profile is first calculated using the values of m and d. The "smoothing" of the profile is then parameterised by incorporation into the model of a variable smoothing length δ. The channel depth at each X value is obtained by taking the depth calculated for the isotropic etch profile averaged over the range of X values corresponding to ±δ. Fitting of the experiment channel profiles then yields the best-fit values of m, d and smoothing length δ. A zero value of δ corresponds to no distortion from the idealised isotropic etch profile whereas a high value indicates that significant smoothing has occurred during either the etching or thermal bonding processes.

It will be appreciated that the method described above can be varied in many ways. Firstly, the method may be used to estimate dimensions of openings in any type of body (so long as the body is transparent to a suitable type of electromagnetic radiation).

Instead of the visible light emitted from the tungsten lamp 10, other types of electromagnetic radiation may be used. Preferably the radiation will be in the range of UV to infra-red.

The method can be used to measure dimensions in the range of 10 μm to 500 μm, which are the most common dimensions of channels in micro-reactors. Dimensions of less than 10 μm and greater than 500 μm may also be measured.

It is preferable to be able to determine a number of absorbances, corresponding to a number of depths, substantially simultaneously. This is made possible by using a CCD camera that allows substantially simultaneous measurement of radiation intensities at a number of areas. However, the method can equally be performed by measuring the radiation intensity at a single area, so as to give a single depth. A series of such single depth determinations may be made sequentially, so as to determine a number of depths in a particular opening.

For a body having an opening of which the dimensions are already known, then the method can be adapted to determine concentrations of an absorbing chemical at different positions in the opening. Clearly, when the extinction co-efficient of the chemical and the dimensions of the opening are known, then intensity values determined as described above may be used to estimate concentration of the chemical. This alternative method may be particularly useful in that it may allow movement and reaction of chemical species in micro-reactors to be estimated. By taking a number of images over time, concentrations of chemical species can be determined, in different areas of the micro-reactor, over time.

An example of use of the alternative method to determine concentrations of a chemical in different regions of a micro-reactor 41 over time will now be described. In this example, the chemical monitored does not react but it does move through the channels of the micro-reactor 41. As the concentrations are monitored over time, the method provides useful information about the movement of the chemical and about mixing of solutions in the micro-reactor 41.

Figure 8:
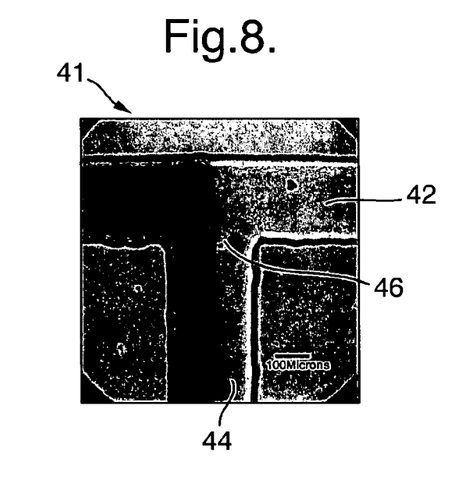
FIG. 8 is a micrograph of part of a micro-reactor.

With reference to FIG. 8, the micro-reactor 41 used in this example is formed from a base plate and an upper block (as for the micro-reactor 26) and has first 42 and second straight channels 44. A first end 46 of the second channel 44 opens into the midpoint of the first channel 42 so that the first and second channels 42,44 together form a "T"-shape. A first reservoir (not shown) lies at and opens into one end of the first channel 42 (at the left end of the first channel 42 as shown in FIG. 8). A second reservoir (not shown) lies at and opens into the other end of the first channel 42 (at the right end of the first channel 42 as shown in FIG. 8). A third reservoir (not shown) lies at and opens into the other end of the second channel 44 (at the bottom of the second channel 44 as shown in FIG. 8). In addition to the channels 42,44 and the reservoirs described above, the micro-reactor 41 also has two small marks (not shown) etched in the upper surface of the base plate (and covered by the upper block) and unconnected with the network of channels and reservoirs. These marks are used as reference marks so that any position within the channels 42,44 can be defined uniquely by its distance from both reference marks.

Firstly, the depths of the channels 42,44, for the whole area of the channels, are determined as described above. The images used to determine the depths also include the two reference marks and this allows the position of each depth measurement to be determined in relation to the two reference marks. This step of determining the depths and allocating positions to the depths need only be performed once for a given micro-reactor (and so when the depths are already known this step does not form part of the alternative method).

The micro-reactor 41 is then clamped immovably to the stage 18 as described above, so that the camera 14 can record images of the portion of the micro-reactor that is of interest and so that the two reference marks are visable in those images.

The channels 42,44 are then filled with a reference solution (methanol) and, after standardisation and optimisation of the resolution, a reference solution image and a dark image are recorded, as described above.

A dye solution (Rose Bengal in methanol) is then introduced into the first reservoir of the micro-reactor 41. Methanol is introduced into the second and third reservoirs. Electrodes are then inserted into the reservoirs, in a known manner, and voltages are applied using the electrodes, also in a known manner. The voltages at the first and second reservoirs are 450V and 452V respectively relative to the third reservoir. The applied voltages cause the dye solution in the first reservoir and the methanol in the second reservoir to move towards the midpoint of the first channel 42 and then along the second channel 42 to the third reservoir. Mixing of the dye solution and the methanol occurs at the midpoint and in the second channel 44.

While the dye solution is moving through the channels a series of dye solution images are recorded using the camera 14 as described above, over time.

Hence, the method involves the recording of a series of dye solution images, a reference solution image and a dark image. Each mean intensity value (as described above) of each dye solution image will have a corresponding mean intensity value in the reference solution image, the dark image and each other dye solution image.

Additionally, the position in the channels corresponding to each mean intensity value is known relative to the two reference marks. As the depths of the channels 42,44 are known for positions relative to the reference marks, each mean intensity value (from each image) can be associated with a depth corresponding to the part of the channel 42,44 through which has passed the light that is measured, after passage through the micro-reactor, so as to give the mean intensity value in question.

Given that, for each mean intensity value in a dye solution image, the corresponding depth is known, and given that the extinction co-efficient of the dye is known the concentration of the dye in different parts of the channels 42,44 can be determined using the equation:

$$\log\left\{\frac{I_{ref} - I_{dark}}{I_{sol} - I_{dark}}\right\} = Cd\varepsilon$$

Figure 9:
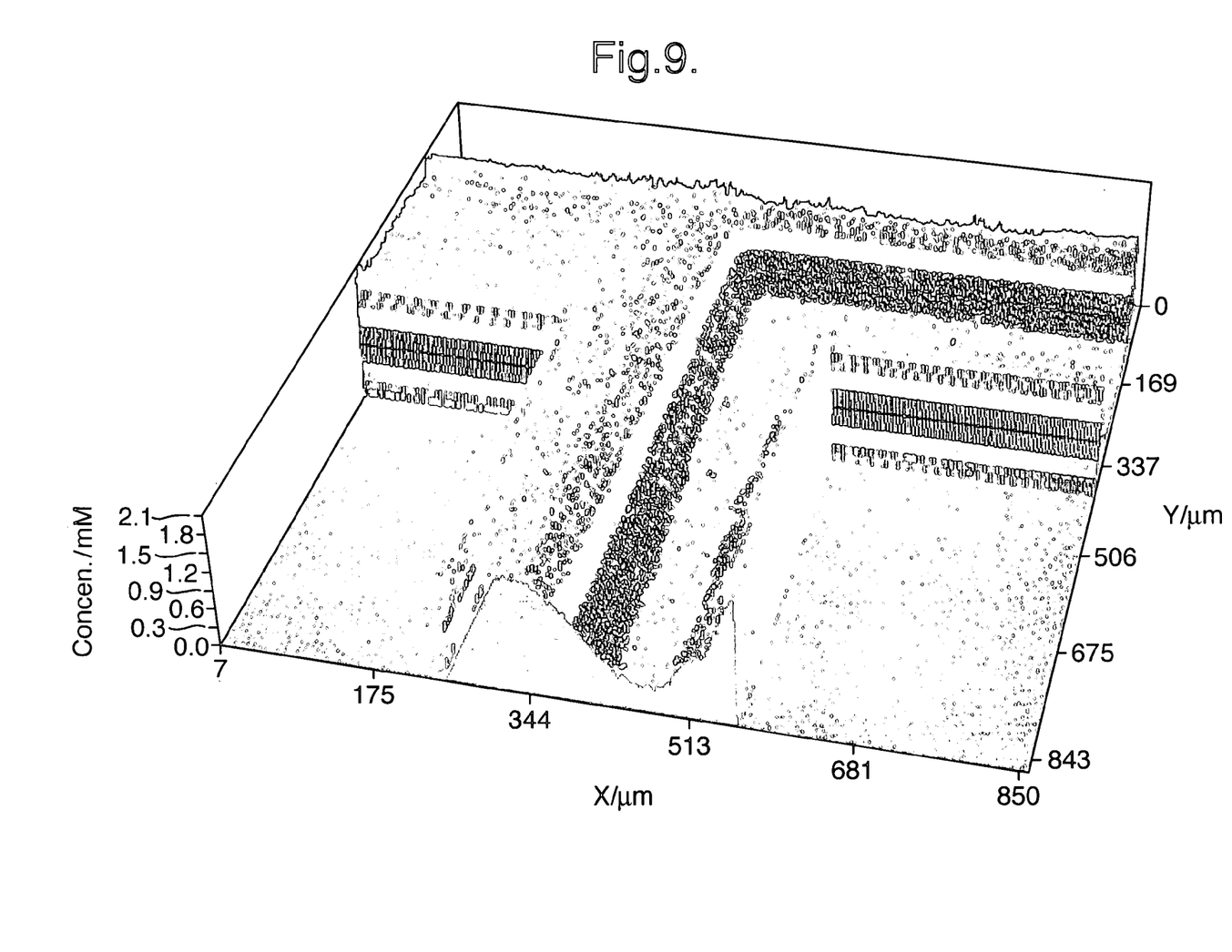
FIG. 9 shows concentrations of a chemical, at a specific moment in time, in various regions of channels contained in the part of the micro-reactor shown in FIG. 8.
Figure 10:
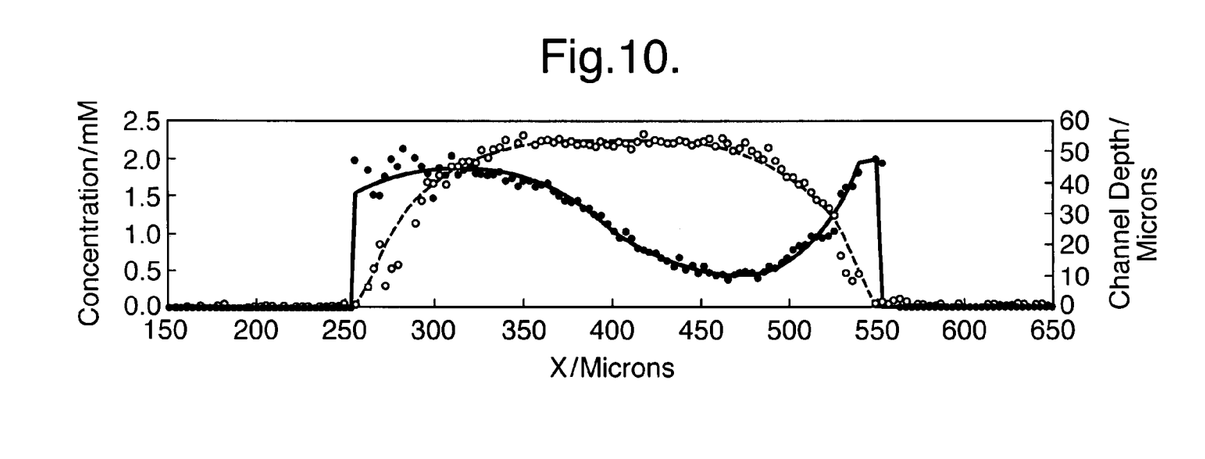
FIG. 10 shows concentrations of a chemical and depth of a channel at a cross-section of a channel of the micro-reactor of FIG. 8.

FIG. 9 shows graphically the concentration of the dye, at different positions, in the portion of the micro-reactor 41 shown in FIG. 8, at a particular moment in time. FIG. 10 shows graphically the concentration of dye (in closed circles) across a cross-section of the second channel 44 (at y=843.1 μm in FIG. 9) at a particular moment in time. The open circles show the depth measurements at that cross-section. Both FIGS. 9 and 10 show that there is a considerable concentration gradient across the second channel 44 and that mixing is by no means immediate at the intersection of the channels 42,44. Both Figures also show that dye is drawn to the sides of the channels—this is thought to be due to electrical charge attraction.

The alternative method described above can be adapted to measure concentration changes occuring due to reactions of chemicals.

The alternative method can be used for micro-reactors having any channel layout. It can also be used for other bodies having openings.

Instead of using visable light other electromagnetic radiation, preferably in the UV to infra-red range may be used.

We claim:

1. A method of estimating dimensions of an opening in a body comprising, filling the opening with a fluid that absorbs an electromagnetic radiation, transmitting said electromagnetic radiation through the body and through the fluid in the opening, determining an intensity of the electromagnetic radiation, after transmission through the fluid, at an area corresponding to a radiation path through the fluid in the opening, and using said intensity to estimate the length of said radiation path, wherein the body comprises a first member having a groove and a second member having a surface, the surface closing the groove to form a channel, the opening being the channel.

2. A method according to claim 1, wherein respective intensities of the electromagnetic radiation, after transmission through the fluid, are determined at a plurality of areas, each area corresponding to a respective radiation path through the fluid in the opening, and using said intensities to estimate the lengths of said radiation paths.

3. A method according to claim 2, wherein the intensities are determined substantially simultaneously.

4. A method according to claim 3, wherein the intensities are measured by a single camera able to measure radiation intensities substantially simultaneously at a plurality of areas.

5. A method according to claim 4, wherein the camera is a CCD camera.

6. A method according to claim 4, wherein the fluid is a solution of a chemical in a solvent, the solvated chemical absorbing the electromagnetic radiation, the camera being used to obtain positionally identical images of the opening when the opening is filled with the solution, when the opening is filled with the solvent, in the absence of electromagnetic radiation, the method including estimating the length of each of said radiation paths using the formula:

$$\log\left\{\frac{I_{ref} - I_{dark}}{I_{sol} - I_{dark}}\right\} = Cd\varepsilon$$

wherein:

$I_{ref}$ is the intensity at an area corresponding to one of said radiation paths for the image when the opening is filled with solvent;

$I_{sol}$ is the intensity at said area for the image when the opening is filled with the solution;

$I_{dark}$ is the intensity at said area for the image in the absence of electromagnetic radiation;

C is the concentration of the chemical in the solution;

$\varepsilon$ is an extinction coefficient of the solvated chemical for the electromagnetic radiation; and d is the length of said one radiation path.

7. A method according to claim 1, wherein the electromagnetic radiation is in the range of UV to infra-red.

8. A method according to claim 1, wherein the fluid has an absorption spectrum for said electromagnetic radiation that has a peak at a predetermined wavelength, a bandpass filter permitting passage of electromagnetic radiation over a wavelength range including said predetermined peak being used to filter said electromagnetic radiation before said determination of said intensity.

9. A method according to claim 1, wherein the fluid has a refractive index for the electromagnetic radiation that is substantially the same as the refractive index of the body for the electromagnetic radiation.

10. A method according to claim 1, wherein the fluid is a liquid.

11. A method according to claim 10, wherein the liquid is not volatile at room temperature.

12. A method according to claim 10, wherein the liquid absorbs the electromagnetic radiation substantially in accordance with the Beer-Lambert Law.

13. A method according to claim 10, wherein the liquid is a solution of a chemical in a solvent, the solvated chemical absorbing the electromagnetic radiation.

14. A method according to claim 13, wherein the liquid has an absorption spectrum for said electromagnetic radiation that has a peak at a predetermined wavelength, a bandpass filter permitting passage of electromagnetic radiation over a wavelength range including said predetermined peak being used to filter said electromagnetic radiation before said determination of said intensity, and wherein the solvent substantially does not absorb the electromagnetic radiation at the predetermined wavelength.

15. A method according to claim 1, wherein the body is a chip-type micro-reactor.

16. A method according to claim 1, wherein the electromagnetic radiation is in the range of visible light.

17. A method of monitoring concentration of a chemical in a fluid filling an opening in a body, the chemical absorbing an electromagnetic radiation, comprising transmitting said electromagnetic radiation through the body and through the fluid in the opening, determining respective intensities of the electromagnetic radiation, after transmission through the fluid, at a plurality of areas corresponding to respective radiation paths through the fluid in the opening, and using said intensities to estimate respective concentrations of the chemical in the radiation paths, wherein the respective concentrations of the chemical and the radiation paths are different from one another, and the body comprises a first member having a groove and a second member having a surface, the surface closing the groove to form a channel, the opening being the channel.

18. A method according to claim 17, wherein the intensities are determined substantially simultaneously.

19. A method according to claim 18, wherein the intensities are measured by a single camera able to measure radiation intensities substantially simultaneously at a plurality of areas.

20. A method according to claim 19, wherein the camera is a CCD camera.

21. A method according to claim 19, wherein the fluid is a solution of the chemical in a solvent, the camera being used to obtain positionally identical images of the opening when the opening is at least partially filled with the solution, when the opening is filled with the solvent, and in the absence of electromagnetic radiation, the method including estimating the concentration of the chemical in each of said radiation paths using the formula:

$$\log\left\{\frac{I_{ref} - I_{dark}}{I_{sol} - I_{dark}}\right\} = Cd\varepsilon$$

wherein:
$I_{ref}$ is the intensity at an area corresponding to one of said radiation paths for the image when the opening is filled with solvent;
$I_{sol}$ is the intensity at said area for the image when the opening is filled with the solution;
$I_{dark}$ is the intensity at said area for the image in the absence of electromagnetic radiation;
C is the concentration of the chemical in the solution;
$\varepsilon$ is an extinction coefficient of the solvated chemical for the electromagnetic radiation; and
d is the length of said one radiation path.

22. A method according to claim 17, wherein the electromagnetic radiation is in the range of UV to infrared.

23. A method according to claim 17, wherein the chemical has an absorption spectrum for said electromagnetic radiation that has a peak at a predetermined wavelength, a bandpass filter permitting passage of electromagnetic radiation over a wavelength range including said predetermined peak being used to filter said electromagnetic radiation before said determination of said intensities.

24. A method according to claim 17, wherein the fluid has a refractive index for the electromagnetic radiation that is substantially the same as the refractive index of the body for the electromagnetic radiation.

25. A method according to claim 17, wherein the fluid is a solution of the chemical in a solvent.

26. A method according to claim 25, wherein the chemical has an absorption spectrum for said electromagnetic radiation that has a peak at a predetermined wavelength, a bandpass filter permitting passage of electromagnetic radiation over a wavelength range including said predetermined peak being used to filter said electromagnetic radiation before said determination of said intensities, and wherein the solvent substantially does not absorb the electromagnetic radiation at the predetermined wavelength.

27. A method according to claim 17, wherein the body is a chip-type micro-reactor.

28. A method according to claim 17, wherein the electromagnetic radiation is in the range of visible light.

* * * * *